United States Patent [19]
Higgins et al.

[11] Patent Number: 4,743,541
[45] Date of Patent: May 10, 1988

[54] LUMINESCENT SUBSTRATE PREPARATION AND ITS USE IN SPECIFIC BINDING ASSAYS

[75] Inventors: Keith W. Higgins, Santa Clara; Christopher R. Brown, San Mateo; John F. Burd, Sunnyvale, all of Calif.

[73] Assignee: Mast Immunosystems, Inc., Palo Alto, Calif.

[21] Appl. No.: 756,039

[22] Filed: Jul. 17, 1985

[51] Int. Cl.$^4$ ............... C07D 237/30; G01N 33/535; G01N 33/543
[52] U.S. Cl. ........................................ 435/7; 435/28; 435/810; 436/501; 436/513; 436/518; 436/805; 544/237
[58] Field of Search ............... 435/7, 8, 28, 810; 436/172, 501, 513, 518, 805; 544/237

[56] References Cited

U.S. PATENT DOCUMENTS

| | | | |
|---|---|---|---|
| 3,256,833 | 3/1966 | Ali et al. | 436/513 |
| 4,011,219 | 3/1977 | Nishii et al. | 544/237 |
| 4,104,029 | 8/1978 | Maier | 436/817 |
| 4,226,993 | 10/1980 | Buckler et al. | 544/237 |
| 4,334,069 | 6/1982 | Buckler et al. | 544/237 |
| 4,459,360 | 7/1984 | Marinkovich | 436/513 |

FOREIGN PATENT DOCUMENTS 0464947  5/1950  Canada .

OTHER PUBLICATIONS

L. J. Bowie, *Meth. Enzymol.* 57, 15–28, 1978.
T. P. Whitehead et al. *Clin. Chem.* 25, 1531–1546, 1979.
L. Fisser "Organic Experiments" (Boston, 1964) p. 240–242.
Journal of American Chemical Society, vol. 56, p. 241 (1934).
"Organic Synthesis" vol. 29, p. 78 (1949).

*Primary Examiner*—Sidney Marantz
*Assistant Examiner*—David A. Saunders
*Attorney, Agent, or Firm*—Townsend and Townsend

[57] ABSTRACT

A luminescent substrate preparation having a concentration of catalytic inhibitors of less than about 100 ppm. The preparation is obtained by heating commercial grade luminol in a basic solution, crystallizing the luminol and separating the luminol crystals from the boiled solution. The heating, crystallization and separation steps are preferably repeated sequentially at least four times, with the starting material for each sequence after the first being the luminol preparation produced in the previous sequence. The luminol preparation has an enhanced pattern of activity, in that light output is substantially constant over a period of at least about one hour, with the intensity of light emitted by the preparation being at least about ten times that of commercially available luminol. Because of these enhanced characteristics, the luminol preparation is particularly adapted for use as a tag in specific binding assays where the concentration of analyte to be detected is low.

13 Claims, No Drawings

LUMINESCENT SUBSTRATE PREPARATION AND ITS USE IN SPECIFIC BINDING ASSAYS

BACKGROUND OF THE INVENTION

This invention relates to luminescent reagents having utility for monitoring specific binding reactions and, more particularly, to a luminol preparation having enhanced light output and stability.

Specific binding assays provide an economical means for detecting and measuring an analyte present in low concentrations in a sample. Specific binding assays are based upon the interaction of two bindable substances, one the analyte and the other a specific binding partner, which specifically recognize each other. Examples of specific binding partners whose interaction can serve as the basis for a specific binding assay include antigens-antibodies, biotin-avidin, nucleic acid probes, enzymes-substrates, enzymes-inhibitors, enzymes-cofactors, chelators-chelates, and cell surface receptor pairs. Assays involving other specifically bindable substances are also known and within the scope of the present invention. Specific binding assays have shown great utility in determining various analytes in biological, medical, environmental, agriculture and industrial applications.

A variety of assays using the principles of the specific binding approach are known, and several have become important diagnostic tools. In one such type of specific binding assay, the immunoassay, the analyte is an antibody, antigen, or hapten, and is made to react with another member of this group. While the background discussion will focus on such immunoassays, this focus is made for clarity of presentation, and is not to be interpreted as limiting of the invention, which is broadly applicable to luminescently labelled specific binding assays.

A variety of labelling reactions have been proposed for use in specific binding assays, including radioactive, enzymatic, chromogenic and luminogenic procedures. In a radioactive labelling procedure, the component conjugated with the specific binding partner is an atom or molecule which emits radioactivity. Chromogenic and luminogenic labelling reactions are chemically more complex, in that several reactants may be involved. The chromophore or lumiphore may itself be the label in the reaction, or a catalyst, typically an enzyme, may be used as the label. When the catalyst is used as the label, it will react with catalytic substrates which in turn produce color or luminescence. The remaining components of the reaction, that is, those not conjugated to the binding partner, are supplied in a chromogenic or luminogenic reagent medium, so that the uniting of the labelled conjugate and the reagent medium results in the desired color change or light emission, respectively.

Luminescent labels are attractive alternatives for use in specific binding assays for a variety of reasons. Luminescence is broadly defined as the production of visible light by atoms that have been excited by the energy produced in a chemical reaction, usually without an associated production of heat. Chemical energy excited electrons in the light-emitting molecules to higher energy states, from which electrons eventually fall to lower energy states with the emission of quanta of energy in the form of visible light. Luminescence is observed in several synthetic chemical compounds and also in naturally occurring biological compounds such as found in fireflies and certain species of fish.

One of the most important families of chemiluminescent molecules are the phthalylhydrazides. The most familiar member of this family is luminol, or 5-amino-2,3-dihydro-1,4-phthalazinedione, which has a gross chemical composition of $C_8H_7N_3O_2$ and a double ring structure with a melting point of about 320° C. Luminol is commercially available from several suppliers and is well characterized. Certain luminol analogs are also chemiluminescent, such as those wherein the position of the amino group is shifted (e.g., isoluminol, the amino group being at the 6 position), or is replaced by other substituents, as well as annelated derivatives and those with substitution in the nonheterocyclic ring. Some luminol analogs produce light more efficiently than does luminol itself, while others have lower efficiency. (As used herein, the term "luminol" encompasses such related species.)

Generally, luminol produces light in an oxidizing reaction, wherein the luminol combines with oxygen or an oxidizer to produce a reaction product and photons at a wavelength of about 425–450 nanometers (nm). The precise reaction formula and the quantum efficiency of light production (that is, the ratio of luminescing molecules to total molecules of the luminescent species) depend upon the medium in which the luminol resides, temperature and other reaction conditions. Typical oxidizers used in conjunction with luminol include oxygen, hydrogen peroxide, hypochloride, iodine, and permanganate.

The oxidation of luminol with the associated production of light occurs rather slowly at ambient temperatures, unless the reaction is catalyzed. A variety of different substances can catalyze the reaction, including organic enzymes (for example, horseradish peroxidase), other organic molecules such as microperoxidase and heme, positive metallic ions such as the cupric ion, and negative ions such as the ferricyanate ion.

Luminescent molecules would appear to be highly desirable as tags in specific binding assays because of their stability, sensitivity, the potential ease of detecting their emitted visible light and their lack of toxicity. Commercial luminol, however, has proven to be unsuitable for such purposes. There exists a need for specific improvements in the light emission characteristics of the reaction for use with such assays. Heretofore, commercial luminol has not shown sufficient activity to be useful to measure analytes at low concentrations in specific binding assays. The light emission intensity of the luminol reaction may be sufficient where high concentrations of catalyst are employed and where highly sophisticated and sensitive photometers are available, but the luminescent intensity has not been sufficient with low concentrations of catalyst and where other detection media such as photographic film or less sensitive photometers are used.

While the luminol reaction therefore offers important potential benefits in the measurement of the presence and amount of a reaction component, for many potential applications the intensity of the emitted light is too low. Further, the light emitted from commercial luminol exhibits an early flash of light without the first few seconds of the initiation of the reaction, followed by a progressive and rapid decrease in light emission over time. The integrated light intensity during any fixed period of time is therefore likely to be different from that measured over any other equal period of time. This variability may result in irreproducibility between tests. Desirably, there would be some period of time during which the light emission from the luminol reaction is relatively constant, so that the measurement of integrated light intensity could begin at different times after initiation of the reaction but within the period of constant light output, without variability of the results. This would eliminate the requirement that the reagents be added to a solution fixed in front of the luminescence detector which puts severe constraints on the light measuring system.

Inhibitors for the catalysts used in luminescent reactions have been reported (Theorell, *The Enzymes*, Vol. II, Part I, p. 397, Academic Press (1951)). However, the need to rigorously remove these inhibitors from luminogenic substrates has heretofore not been appreciated. We have discovered that rigorous removal of inhibitors from the luminescent substrates produces substantial improvement in the resulting sensitivity and reproducibility in specific binding assays. This is especially important when measuring low concentrations of analyte which necessitates low concentrations of catalyst.

There therefore exists a need for an improved luminescent substrate for use in specific binding assays and other applications. The improved luminescent substrate should exhibit an increased unit light intensity output per molecule of reacting luminescent substrate to allow its use as a tag in specific binding assays such as immunoassays where the concentration of analyte is low. The improved luminescent substrate should exhibit a period of substantially constant light output that would allow repetition of test procedures and eliminate many constraints on the user and the light detection system. The present invention fulfills these needs, and further provides related advantages.

SUMMARY OF THE INVENTION

The present invention provides an improved luminescent substrate preparation exemplified by a luminol preparation, its method of preparation and its use in luminescent assays. The luminol preparation exhibits an increased light output of about at least a factor of ten, as compared with typical samples of commercially available luminol. Further, the luminol preparation also exhibits a more uniform light output as a function of time than untreated luminol when used in a specific binding assay.

In accordance with the present invention, a method for making the luminol preparation from untreated commercial luminol is provided which comprises the steps of furnishing commercial luminol; dissolving the luminol in an alkaline solution; heating the solution; and separating crystals of the luminol preparation from the heated solution. The steps of dissolving, heating and separating are preferably repeated sequentially, in each sequence using as the luminol starting material the crystals prepared in the prior sequence. In a preferred embodiment, it is found that four repetitions provide a significantly enhanced luminol preparation, and that fewer or greater repetitions may be justified, given the constraints required for the particular assay.

It is believed that the enhanced characteristics of the luminol preparation result from a reduction in the level of substances which inhibit chemiluminescent reactions, specifically by inhibiting the activity of catalysts, e.g., peroxidase, used in monitoring specific binding assays. For example, hydrazine and sulfide ions inhibit the peroxidase reaction, and that one or both such inhibitors as well as others may be present in commercially available luminol as a result of the synthesis procedure used in the preparation of luminol.

In accordance with another aspect of the invention, a luminol preparation is provided which has a concentration of inhibitors of less than 100 parts per million. The luminol preparation exhibits a unit light output per molecule of reacting luminol approximately ten times greater than that of commercially prepared, untreated luminol. The increased unit light output allows more sensitive measurements of chemical reactions in qualitative and quantitative tests. Moreover, whereas the luminescence emitted by commercially available, untreated luminol shows a substantial decrease in light emission over time after initiation of the reaction, the luminol preparation reported herein shows a dramatic improvement in that the luminescence emission over time does not substantially decrease. It will be appreciated that these enhancements to luminol constitute an important improvement in the art of luminescent reactions, particularly where such reactions are used to measure low concentrations of analyte in specific binding assays.

In accordance with a further aspect of the invention, the luminol preparation is used to monitor luminescent specific binding assays. Until now, the most commonly used tags for monitoring specific binding assays have been various radioactive ions, such as $^{125}I$. Because of the safety problems involved in handling and disposing of radioactive materials, it is highly desirable to utilize alternative tagging materials. Luminescent materials, which predictably emit light under certain conditions, are an obvious choice and have been used for certain applications. Commercial luminol has until now been inappropriate for use in particular types of assays, such as specific binding assays, where the concentration of analytes to be measured is low, because of its low level of light emission per molecule. The luminol preparation of the present invention, however, possesses enhanced emission characteristics which render it useful in such specific binding assays.

In a preferred embodiment, the luminol preparation is used to monitor the presence of antibodies specific for various allergens (IgE) in the serum of patients. Allergens are immobilized on a solid support, such as cotton threads, and contacted with a sample of human serum to allow binding between the allergens and corresponding antibodies. The solid support is then contacted with a solution containing anti-IgE antibodies which have been labelled with peroxidase. After incubation to allowing binding between any IgE present and the anti-IgE antibody, the threads are contacted with a solution containing luminol and peroxide. In the presence of the catalyst peroxidase, the luminol emits light, permitting localization of the tagged anti-human antibody and, ergo, the IgE.

It will be appreciated that these enhancements of luminol constitute an important improvement in the art of luminescent reactions. Other features and advantages of the present invention will become apparent from the following more detailed description which illustrates, by way of example, the principles of the invention.

DETAILED DESCRIPTION OF THE PREFERRED EMBODIMENT

The synthesis of luminol is reported in references listed in entry number 5413 of the Merck Index, which is herein incorporated by reference, and need not be set forth in detail herein. However, common to the synthesis procedures is the use of hydrazine and sulfur containing compounds. For example, in Huntress, *J. Am. Chem. Soc.* 56: 241 (1934), hydrazine is used to synthesize 3-nitrophthalhydrazide, and this compound is then dissolved in ammonium sulfide during the preparation of luminol. In the procedure set forth in Redemann, *Org. Syn.* 29: 78, 8 (1949), hydrazine sulfate is used to prepare a mixture of sodium sulfate and 5-nitro-2,3, dihydro-1,4-phthalazinedione, and this compound is converted to luminol, in part through the use of sodium hydrosulfite dihydrate. Thus, in both synthesis procedures, hydrazine and sulfur containing compounds are intentionally utilized in synthesizing the luminol. As noted in the Redemann discussion, the intermediate product may contain small amounts of inorganic salts, which may be carried through the final luminol product.

Luminol is available commercially as crystals or as a fine yellowish powder from several sources, including: Sigma Chemical Company, St. Louis, MO; Aldrich Chemical Company, Inc., Milwaukee, WI; Mallinckrodt, St. Louis, MO; Fisher Scientific Company, Pittsburgh, PA. The sources do not disclose the synthesis procedure, and it is therefore not possible to state with certainty the procedure used. The procedure may be one of those disclosed publicly, or yet other synthesis procedures may be followed. One important feature of the present invention is the ability to improve a variety of commercially available, untreated luminols, without any knowledge of the procedure used in synthesizing the luminol.

Regardless of the synthesis procedures used and the reasons underlying the effect, the user of commercially purchased, untreated luminol must contend with a low level of light output from the material. While these phenomena may be acceptable to some users of luminol, in sensitive quantitative analysis procedures the variability and low light output can pose significant problems. These problems could conceivably be overcome through the use of specialized measurement apparatus or, as in the present case, by improving luminol so as to avoid the problems. As used herein, the term "luminol preparation" refers to a material which is prepared from untreated luminol, typically commercially available luminol, and exhibits intensified unit light output.

In accordance with the invention, a luminol preparation is prepared by furnishing commercially prepared, untreated luminol, dissolving the luminol in an alkali solution to form a crude solution, boiling the crude solution to form a heated luminol solution, and separating activated luminol crystals from the heated luminol solution. This procedure is repeated as necessary to achieve a luminol preparation of sufficient quality to accommodate the constraints dictated by the specific binding assay in which it is used. The luminol preparation can be used as a tag in standard specific binding assay formats, such as those disclosed in Maggio, *Enzyme Immunoassay*, CRC Press (1980), which is incorporated herein by reference.

EXAMPLE 1

PREPARATION OF LUMINOL TO REMOVE CATALYTIC INHIBITORS

In a preferred activation procedure for preparing approximately 18–28 grams of activated luminol from 100 grams of untreated, commercially prepared luminol (Mallinckrodt, St. Louis, MO), 22.6 grams of sodium hydroxide is dissolved in 188 milliliters of distilled water. One hundred grams of untreated luminol is added to this sodium hydroxide solution and stirred until dissolved, to achieve an alkaline pH, preferably between 11 and 14 and most preferably 12–13. A second volume of 188 milliliters of distilled water is then added to the mixture. The mixture is heated in a glass container to the boiling point, about 100° C., for a period of time of from about 60 to 120 minutes. The boiled solution is cooled to the temperature range of from about 50° to about 80° C., and poured through a 5 micron membrane filter. The filtered solution is cooled to a temperature of from about 0° C. to about −50° C., to initiate the growth of crystals in the container. The crystals are allowed to grow for at least 1 hour, and preferably 8 hours, after crystallization first begins, and then filtered to collect the crystals. The crystals are washed with cold anhydrous alcohol and dried. They are then dissolved in water and the solution acidified with glacial acetic acid to pH 5–6. At this point, the solution becomes pasty and must be stirred well to insure a uniform distribution and pH. The luminol paste is filtered and washed with cold water (about 4° C.) until acetic acid has been washed away or the filtrate returns to pH 7.0.

The unit light intensity output of the luminol preparation is observed to be substantially greater than that of the untreated luminol. The light intensity output may be further improved by repeating the treatment procedure previously described.

As is apparent, the treatment sequence may be repeated as many times as desired, with the ultimate end point being determined by a trade-off between improved light output properties, the reduced yield of activated luminol with each succeeding sequence and the particular requirements of the specific binding assay being measured. A total of four treatment sequences is presently preferred, based upon the improved properties of the thus prepared luminol, considerations of the yield of the process and the particulars of the specific binding assay.

EXAMPLE 2

LIGHT EMISSION OF LUMINOL PREPARATION

A standardized test procedure for measuring luminol light output has been established. To 0.5 ml of 50 mM borate buffer, pH 9.4, are added 0.5 ml of 40 mM luminol in 45 mM NaOH, pH 11.0; 0.5 ml of 4 mM hydrogen peroxide in 0.01M phosphate buffered saline (PBS), pH 7.0; 0.4 ml of deionized water; and 0.1 ml of 200 mU/ml horseradish peroxidase (HRP) to yield a final 2.0 ml volume containing; 10 mM luminol; 1 mM $H_2O_2$; 12.5 mM borate buffer, pH 9.4; and 20 mU HRP in an aqueous solution having a final pH of 9.4. The enzyme HRP is added last, the solution mixed and relative intensity readings taken on an Ames Fluorocolorimeter (Miles Labs, Inc., Elkhart, IN) at various time points from 1 minute to 2 hours.

The following table, Table I, illustrates the light output for luminol prepared by repeating the treatment procedure one to four times, compared to untreated luminol. Increasing the number of treatment sequences performed results in a continuing increase in the unit light intensity output of the activated luminol when tested in the standardized testing procedure. Additionally, the uniformity of the light intensity over time improves, and the luminol subjected to four repetitions of the treatment sequence exhibits a substantially uniform unit light intensity from about 5 minutes to about 120 minutes after the start of the reaction, as illustrated in Table II. With this information, it is possible for the user of luminol to begin the recording of the reaction at any time during which the light intensity remains constant.

TABLE I

|  | Luminescent Intensity Units |
|---|---|
| Commercial Luminol | 0.016 |
| First crystallization | 0.029 |
| Second crystallization | 0.622 |
| Third crystallization | 1.036 |
| Fourth crystallization | 1.046 |

TABLE II

IMPROVEMENT IN LUMINESCENT INTENSITY OVER TIME

| Time After Initiation of Reaction (min.) | Luminescent Intensity Units | |
|---|---|---|
|  | Activated Luminol | Commercial Luminol |
| 5 | 1.02 | 0.013 |
| 10 | 0.95 | 0.012 |
| 20 | 0.95 | 0.011 |
| 30 | 0.96 | 0.011 |
| 40 | 0.97 | 0.010 |
| 50 | 0.98 | 0.008 |
| 60 | 0.98 | 0.007 |
| 70 | 0.98 | 0.006 |
| 80 | 0.98 | 0.005 |
| 90 | 0.97 | 0.005 |
| 100 | 0.97 | 0.005 |
| 110 | 0.96 | 0.005 |
| 120 | 0.96 | 0.005 |

EXAMPLE 3

EFFECT OF INHIBITORS ON LUMINESCENT REACTION

The chemical synthesis of luminol and other luminescent substrates use chemicals which can inhibit the catalysts used in luminescent reactions. Two of these inhibitory chemicals known to be used in luminol synthesis were added back to a luminescent reaction using the luminol prepared in Example 1 above. The reaction conditions were as detailed in the example using the light emission at 30 minutes as the indicator for the reaction, except that varying concentrations of ammonium sulfide, hydrazine sulfate and ammonium sulfate were added to the reactions prior to the addition of the catalyst. The results were as indicated in Table III:

TABLE III

|  | % Reaction |
|---|---|
| No Additions | 100% |
| Ammonium Sulfide |  |
| 1 ppm | 94% |
| 10 ppm | 90% |
| 100 ppm | 47.5% |
| 1,000 ppm | 11.1% |
| 10,000 ppm | 9.6% |
| 100,000 ppm | .5% |
| Hydrazine Sulfate |  |
| 1 ppm | 92.5% |
| 10 ppm | 86.2% |
| 100 ppm | 5.6% |
| 1,000 ppm | 3.6% |
| 10,000 ppm | 2.5% |
| 100,000 ppm | 1% |
| Ammonium Sulfate |  |
| 1 ppm | 100% |
| 10 ppm | 100% |
| 100 ppm | 100% |
| 1,000 ppm | 100% |
| 10,000 ppm | 100% |
| 100,000 ppm | 100% |

As shown, the presence of sulfide and hydrazine ions drastically inhibits the luminescence yield in the reaction. The presence of their counter ions, as demonstrated by the ammonium sulfate reactions, had no effect.

This experiment demonstrates that the luminol must be at least 99.99% free of inhibiting substances in order to obtain the sensitivity required in specific binding assays measuring very low concentrations of analytes.

EXAMPLE 4

USE OF LUMINOL PREPARATION

The luminol preparation may be successfully used to detect the presence of a specific binding reaction as, for example, in a standard immunoassay format. In a preferred embodiment, allergens to which a patient is suspected of having a hypersensitivity are immobilized on a solid support, such as cotton threads. A series of such threads, each coated with a different allergen can then be mounted together in a spaced relationship for simultaneous exposure to a serum sample of the patient. The serum is then removed and the threads washed. The threads are then exposed to a solution containing anti-human IgE antibodies which have been labelled with a component of the luminol reaction, preferably the catalyst horseradish peroxidase, and any excess washed off. The threads are then exposed to a solution containing the treated luminol preparation and peroxide. Any horseradish peroxidase conjugated anti-human IgE linked to the threads will catalyze a localized chemiluminescent reaction resulting in light emission from the treated luminol. The relative amount of anti-human IgE linked to an individual thread can be determined by monitoring the light emitted adjacent the thread. Because of the enhanced emission and stability of the treated luminol, the amount of light output can be monitored by exposing photographic film, such as Polaroid Type 57 to the threads in solution. The degree of exposure of the film indicates the amount of anti-human IgE and therefore the amount of IgE complementary to each allergen. The demonstration of the use of the activated luminol preparation in a specific binding assay is found in Brown, *Clin. Chem.*, 31/9, 1500–1505 (1985).

While the following explanation is not intended as binding, it is believed that the treatment sequence described above improves the light-emitting efficiency of luminol by reducing the level of trace quantities of substances which inhibit the luminol light-producing reaction. Specifically, inhibition studies presented herein show that hydrazine and sulfide ions, when present in amounts greater than about 100 ppm in the luminol, can inhibit the production of light in the catalyzed luminol oxidation reaction. Since both hydrazine and sulfur-containing compounds are utilized in the synthesis of luminol, it is quite possible that trace quantities of these materials might remain in the crystals after synthesis. Because of the relatively small amounts of impurities that can reduce light output and the possibility of minor deviations from synthesis procedures, it is also quite possible that the quantities of these inhibitors might vary among batches, suppliers, and synthesis techniques. Removal of the inhibitors thus allows the catalyzed oxidation of luminol to proceed with increased unit light intensity.

As will now be appreciated, the activated luminol preparation and the process of making same of the present invention provide an approach for achieving increased unit light intensity in the catalyzed oxidation of luminol, and also increased uniformity of light output with time. The process sequence for treating the luminol is relatively simple and does not involve complex technology or dangerous chemicals. The light intensity of the catalyzed luminol oxidation reaction is multiplied by a factor of at least about ten, thus increasing its sensitivity, decreasing the time necessary for measurements of the light intensity, and allowing experiments or studies to be repeated at constant light output if an error is made in the first measurement. Those skilled in the art will recognize that variations of the preparation procedures described herein may be made within the spirit and scope of the invention. In particular, the process for activating the luminol may be varied within the broad scope of the disclosure, yet achieve substantially the same results in activating the luminol for improved uniformity and increased light output intensity. Accordingly, the invention is not to be limited except as by the appended claims.

We claim:

1. A process for improving the luminescent duration and output of ligand-free phthalylhydrazide derivatives serving as luminescent substrates in peroxidase catalyzed reactions comprising the steps of repeatedly dissolving and recrystallizing the derivatives until sulphide and hydrazine levels are less than about 100 ppm.

2. The process of claim 1 wherein the substrate is luminol.

3. A process according to claim 2 wherein the recrystallization comprises the steps of:
   (a) heating a mixture of luminol and peroxidase inhibitors in an alkaline solution to dissolve the luminol; and
   (b) separating from said solution purified luminol, wherein the purified luminol contains catalytic inhibitors selected from the group consisting of hydrazine and sulfide in a concentration of less than about 100 ppm.

4. The process of claim 3, wherein said alkaline solution comprises sodium hydroxide.

5. The process of claim 4, wherein the concentration of said sodium hydroxide is about 1.5 molar.

6. The process of claim 3, wherein said heating step comprises boiling for a time of from about 60 to about 120 minutes.

7. The process of claim 3, wherein said step of separating includes the substeps of:
   a. filtering the heated solution;
   b. crystallizing the filtered solution by cooling;
   c. collecting crystals obtained from said step of crystallizing;
   d. treating said crystals with acid.

8. A process for detecting an analyte in a test solution based upon a specific binding assay monitored by a luminescent reaction, comprising:
   a. introducing to the analyte a specific binding partner thereof, said specific binding partner being conjugated to a peroxidase catalyst of the luminescent reaction;
   b. contacting luminol to said specific binding partner in the presence of the other components of the luminescent reaction, and in the absence of peroxidase catalytic inhibitors that exceed a concentration of 100 ppm., said inhibitors selected from the group consisting of hydrazine and sulfide; and
   c. monitoring light emitted from said luminescent reaction so as to determine whether said specific binding partner is bound to said analyte.

9. The process of claim 8, wherein said analyte is selected from the group consisting of antigens, haptens and antibodies.

10. The process of claim 8, wherein said analyte is IgE or anti-IgE.

11. A composition of matter for use in binding assays comprising:
    (a) a ligand-free, luminescent substrate that is a phthalylhydrazide derivative; and
    (b) catalytic inhibitors of peroxidase selected from the group consisting of hydrazine and sulfide in a concentration of less than about 100 ppm.

12. The composition of matter as recited in claim 11, wherein the phthalylhydrazide derivative is luminol.

13. A specific binding reaction assay kit for determining the presence of analytes in a test liquid, comprising
    a. a test chamber having means for introducing liquid into said test chamber, said test chamber having located therein at least one test surface having fixed thereto a binding partner for an analyte suspected of being present in the test liquid;
    b. a first liquid component having therein a species specifically reactive with analytes in the test fluid, said species being conjugated with a peroxidase catalyst of a luminescent reaction; and
    c. a second liquid component in a separate container from the first liquid component comprising a luminol preparation having catalytic inhibitors of peroxidase selected from the group consisting of hydrazine and sulfide in a concentration of less than about 100 ppm.

* * * * *